United States Patent
Skarsgard et al.

(10) Patent No.: US 11,497,893 B2
(45) Date of Patent: Nov. 15, 2022

(54) DEVICE FOR STABILIZING CATHETERS AND METHOD OF USE THEREOF

(71) Applicant: Vesalius Cardiovascular Inc., Vancouver (CA)

(72) Inventors: Peter Lloyd Skarsgard, Vancouver (CA); Joash Gomes, Vancouver (CA)

(73) Assignee: Vesalius Cardiovascular Inc., Vancouver (CA)

( * ) Notice: Subject to any disclaimer, the term of this patent is extended or adjusted under 35 U.S.C. 154(b) by 0 days.

(21) Appl. No.: 17/836,803

(22) Filed: Jun. 9, 2022

(65) Prior Publication Data
US 2022/0296858 A1    Sep. 22, 2022

Related U.S. Application Data

(63) Continuation of application No. PCT/CA2021/051790, filed on Dec. 13, 2021.
(Continued)

(51) Int. Cl.
*A61M 25/04* (2006.01)
*A61F 2/24* (2006.01)

(52) U.S. Cl.
CPC .......... *A61M 25/04* (2013.01); *A61F 2/2466* (2013.01); *A61M 2210/125* (2013.01)

(58) Field of Classification Search
CPC .............................. A61M 25/04; A61F 2/2466
See application file for complete search history.

(56) References Cited

U.S. PATENT DOCUMENTS

| 7,438,714 B2 | 10/2008 | Phan |
| 7,753,906 B2 | 7/2010 | Esposito |

(Continued)

FOREIGN PATENT DOCUMENTS

| EP | 0943302 B1 | 10/2005 |
| WO | 2011069025 A1 | 6/2011 |

(Continued)

*Primary Examiner* — Richard G Louis
(74) *Attorney, Agent, or Firm* — Oyen Wiggs Green & Mutala LLP

(57) ABSTRACT

A device for stabilizing catheters such as delivery catheters is disclosed. The device includes a radially expandable structure which extends from a proximal end to an opposing distal end. The expandable structure is secured to a stabilizer catheter at its proximal end. The device includes means to position the delivery catheter relative to the expandable structure. The means may include one or more attachment members arranged to extend distally from the distal end of the expandable structure. Each attachment member is coupleable to a connector projecting near a distal tip of the delivery catheter. The means may alternatively include one or more sleeves, each arranged for the respective one of the delivery catheters to insert therethrough. A retractable catheter sheath is moveable along the longitudinal axis of the expandable structure to extend the expandable structure between a compressed configuration and an expanded configuration. A kit for stabilizing catheters is also enclosed. The kit includes a delivery catheter. The delivery catheter may comprise a connector projecting near a distal end thereof for coupling the attachment member. A method of use of the device for the delivery of biocompatible materials is also disclosed.

12 Claims, 10 Drawing Sheets

Related U.S. Application Data

(60) Provisional application No. 63/127,471, filed on Dec. 18, 2020.

(56) References Cited

U.S. PATENT DOCUMENTS

| | | |
|---|---|---|
| 7,988,646 B2 | 8/2011 | Taber |
| 8,475,487 B2 | 7/2013 | Bonnette et al. |
| 8,512,398 B2 | 8/2013 | Alkhatib |
| 8,876,892 B2 | 11/2014 | Tran et al. |
| 10,478,297 B2 | 11/2019 | Ahlberg et al. |
| 2006/0155366 A1 | 7/2006 | Laduca et al. |
| 2008/0045982 A1 | 2/2008 | To et al. |
| 2015/0081005 A1* | 3/2015 | Headley, Jr. ............ A61F 2/966 623/1.11 |

FOREIGN PATENT DOCUMENTS

| | | |
|---|---|---|
| WO | 2012030587 A1 | 3/2012 |
| WO | 2019213215 A1 | 11/2019 |

\* cited by examiner

DEVICE FOR STABILIZING CATHETERS AND METHOD OF USE THEREOF

CROSS-REFERENCE TO RELATED APPLICATION

This application is a continuation of PCT application No. PCT/CA2021/051790 filed 13 Dec. 2021, which claims priority from US application No. 63/127,471 filed 18 Dec. 2020 and entitled DEVICE FOR STABILIZING CATHETERS AND METHOD OF USE THEREOF which is hereby incorporated herein by reference for all purposes. For purposes of the United States of America, this application claims the benefit under 35 U.S.C. § 119 of US application No. 63/127,471 filed 18 Dec. 2020 and entitled DEVICE FOR STABILIZING CATHETERS AND METHOD OF USE THEREOF.

FIELD OF THE INVENTION

The invention pertains to devices for stabilizing catheters, and methods of using such devices for delivery of biocompatible materials into the heart of a subject.

BACKGROUND OF THE INVENTION

It is known in the art to use catheters for delivery of biocompatible materials into tissues of a subject. For example, it is known in the field of cardiology to use anchor delivery catheters to deliver ventricular anchors in the myocardium in the left ventricle of the heart. It is desirable for a device to stabilize delivery catheters which can provide for precise, controlled and/or atraumatic delivery of biocompatible materials into a specific implantation location in the subject.

SUMMARY

One aspect of the invention provides a device for stabilizing catheters, such as delivery catheters. The device has a radially expandable structure. The expandable structure has a proximal end extending to an opposing distal end. The distal end is defined by a distal edge. The distal edge may for example have a circular or elliptical shape. The device includes means for positioning one or more delivery catheters relative to the expandable structure. In some embodiments, such means includes one or more attachment members arranged to extend distally from a point along the distal edge of the expandable structure. The one or more attachment members are each coupleable to a respective one of a connector projecting near the distal tips of one or more delivery catheters for securing the delivery catheters to the expandable structure. The distal tips may be positioned at a point equal to or greater than a radial limit of the expandable structure. In other embodiments, such means includes one or more sleeves extending from a proximal end to a distal end. One or both of the proximal end and the distal end of the sleeves are secured to the expandable structure, such as by welding. Each one of the delivery catheters is insertable through a respective one of the sleeves. Means are provided to extend the expandable structure between the expanded and compressed configurations. The means may comprise a retractable catheter sheath. Selective movement of the retractable catheter sheath along a longitudinal axis of the expandable structure extends the expandable structure between the expanded and compressed configurations.

Another aspect of the invention provides a kit for stabilizing catheters. The kit comprises the device for stabilizing catheters, and one or more delivery catheters. The one or more delivery catheters may include a connector, each of which is arranged to couple to an attachment member. The connector may be arranged to project from a surface of the delivery catheter near a distal tip of the catheter.

Another aspect of the invention provides a method for using the device to deliver biocompatible materials to a body of a subject. In an example use embodiment, the device is used to deliver ventricular anchors in the myocardium of the left ventricle of the heart. The method optionally involves securing an expandable structure to a stabilizer catheter and/or one or more delivery catheters to form a device. The device is advanced into the body within a region proximate to the desired implantation location. The expandable structure is radially expanded within the region. The method may first involve partially expanding the expandable structure. The partially expanded expandable structure may be rotated to position the respective distal tips of the one or more delivery catheters at the desired implantation location. When the distal tips are precisely positioned, the expandable structure may then be fully expanded. The fully expanded expandable structure contacts the surfaces within the region in order to stabilize the delivery catheter for controlled delivery of the biocompatible materials into the specific implantation location. After delivery of the biocompatible materials, the expandable structure is fully compressed prior to withdrawal of the catheter apparatus from the body of the subject.

Further aspects of the invention and features of specific embodiments of the invention are described below.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DETAILED DESCRIPTION

The invention provides a device for stabilizing catheters. The device comprises an expandable structure that is radially expandable. The device may be used to stabilize catheters for the delivery of biocompatible materials into tissues within a human body. An example of use of the device is to stabilize a catheter for the delivery of anchors within the mycocardium of the left ventricles of the heart. The device stabilizes the delivery catheter by radially extending the expandable structure into an expanded configuration, allowing the expandable structure to be in contact against surfaces surrounding the desired implantation location. Such contact creates a state which allows the delivery catheter and the specific implantation location to move simultaneously. The simultaneous movement advantageously allows for controlled and atraumatic delivery of the anchors and other desired biocompatible materials into a specific implantation location while the heart is beating.

Figure 1:
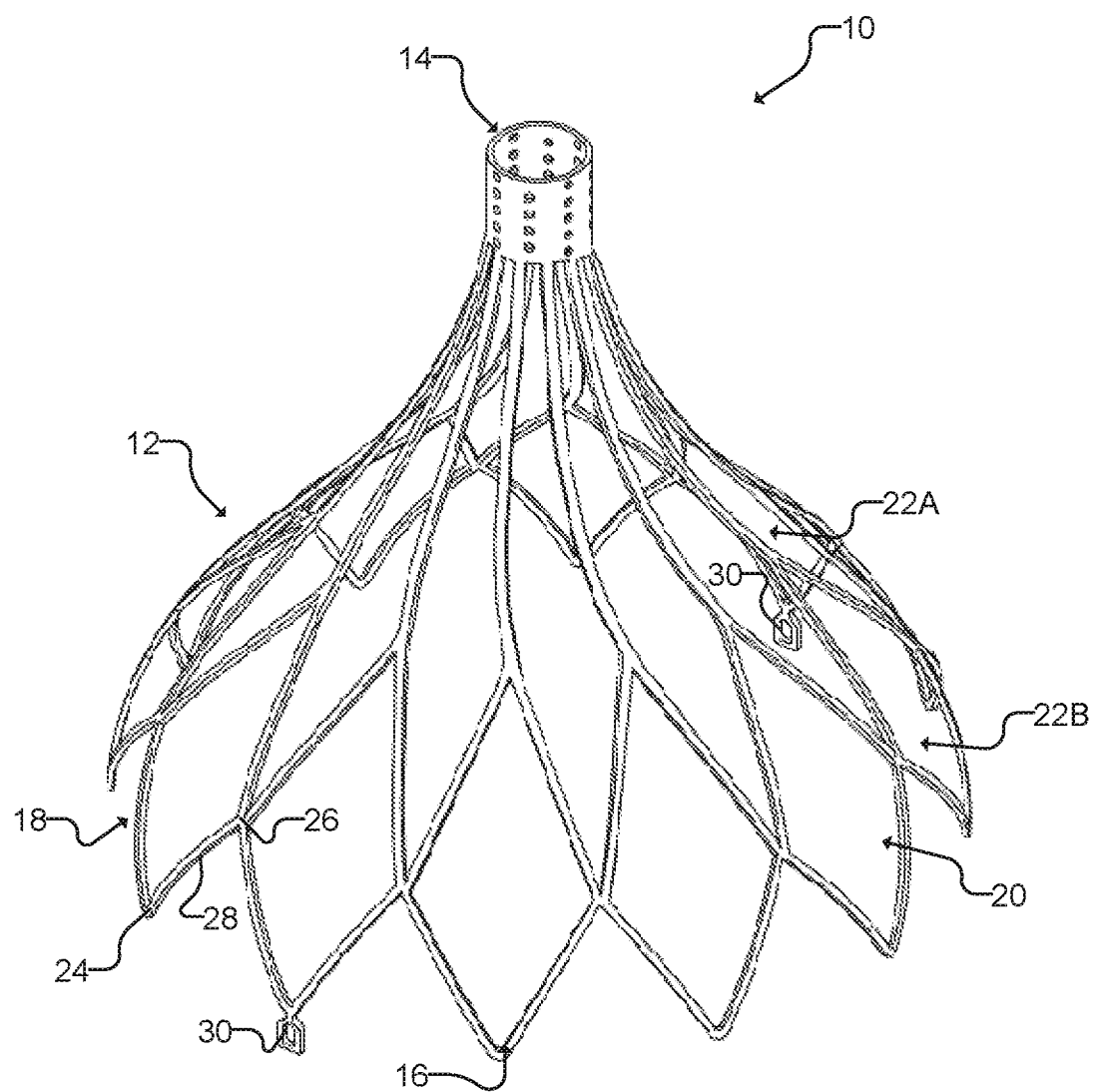
FIG. 1 is an isolated perspective view of a device according to a first example embodiment, showing an expandable structure in an expanded configuration.
Figure 2:
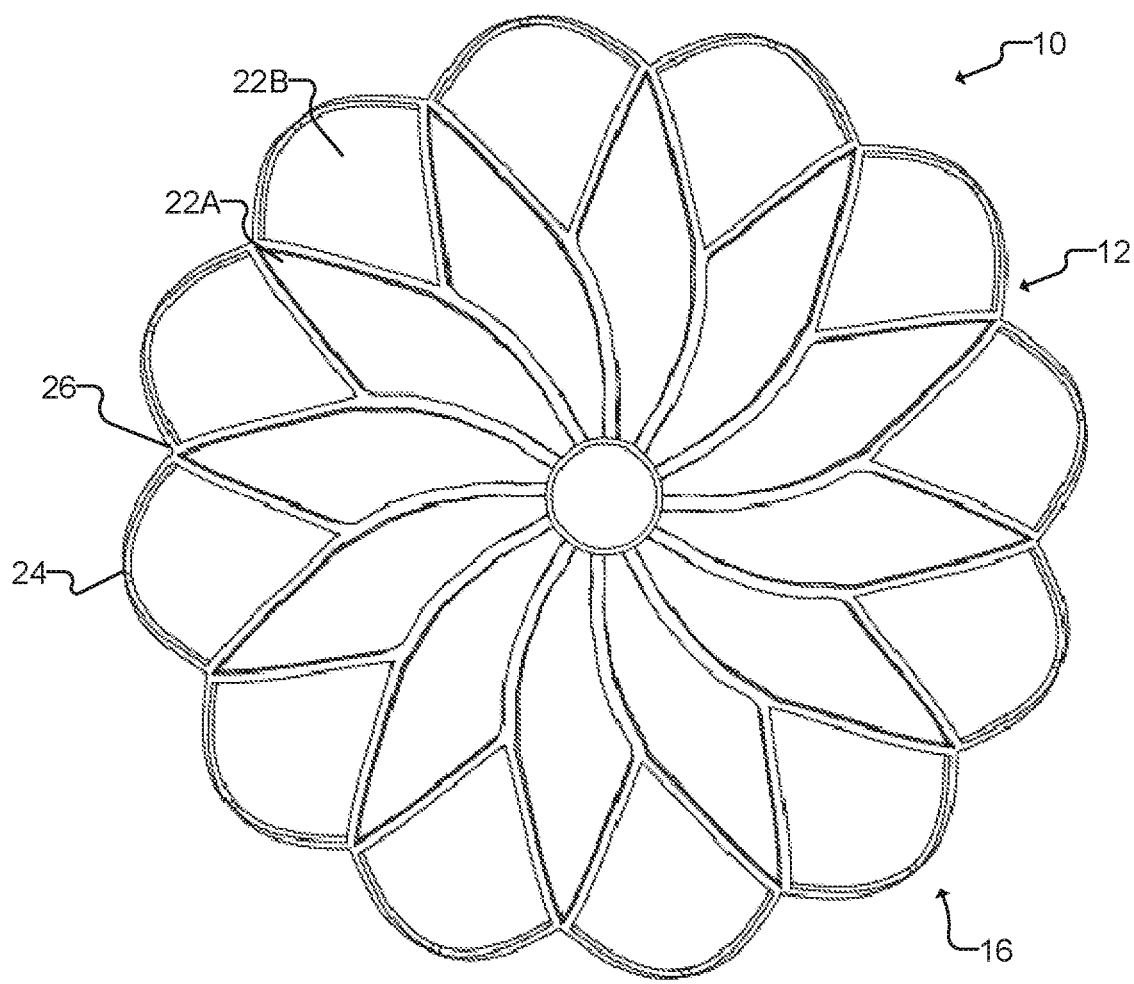
FIG. 2 is an isolated bottom plan view of the device of FIG. 1.

Referring to FIGS. 1 and 2, in one embodiment the device of the invention is a device for stabilizing catheters 10. The device 10 has an expandable structure 12 with a proximal end 14 extending to an opposing distal end 16 along a longitudinal axis of the stabilizer 10. In some embodiments, a radius of the distal end 16 is greater than a radius of the proximal end 14. The distal end 16 may be defined by a distal edge 18. The distal edge 18 may have a closed curve shape. In some embodiments, the distal edge 18 has a circular or an elliptical shape.

The expandable structure 12 comprises a plurality of closed cells 20 arranged radially in one or more rows between the proximal 14 and distal 16 ends. In an example embodiment, the closed cells 20 are arranged in a first row 22A and a second row 22B between the proximal 14 and distal 16 ends. The first row 22A is proximate to the proximal end 14, and the second row 22B is proximate to the distal end 16. Each of the closed cells 20 is defined by an area, i.e., the space enclosed by each of the closed cells 20 in the plane defined by an outer surface of the expandable structure 12. In an example embodiment, the average area of each of the closed cells 20 in the first row 22A is greater than the average area of each of the closed cells 20 in the second row 22B.

In some embodiments, the closed cells 20 in the second row 22B each has a diamond-shape. In such embodiments, the distal edge 18 has alternating sets of first terminal ends 24 and second terminal ends 26. Each of the first 24 and second 26 terminal ends are connected by a diagonal element 28. The first terminal ends 24 may be distally positioned from the second terminal ends 26. The average distance between the proximal end 14 of the expandable structure 12 and each of the first terminal ends 24 may be greater than the average distance between the proximal end 14 of the expandable structure 12 and each of the second terminal ends 26.

Figure 3:
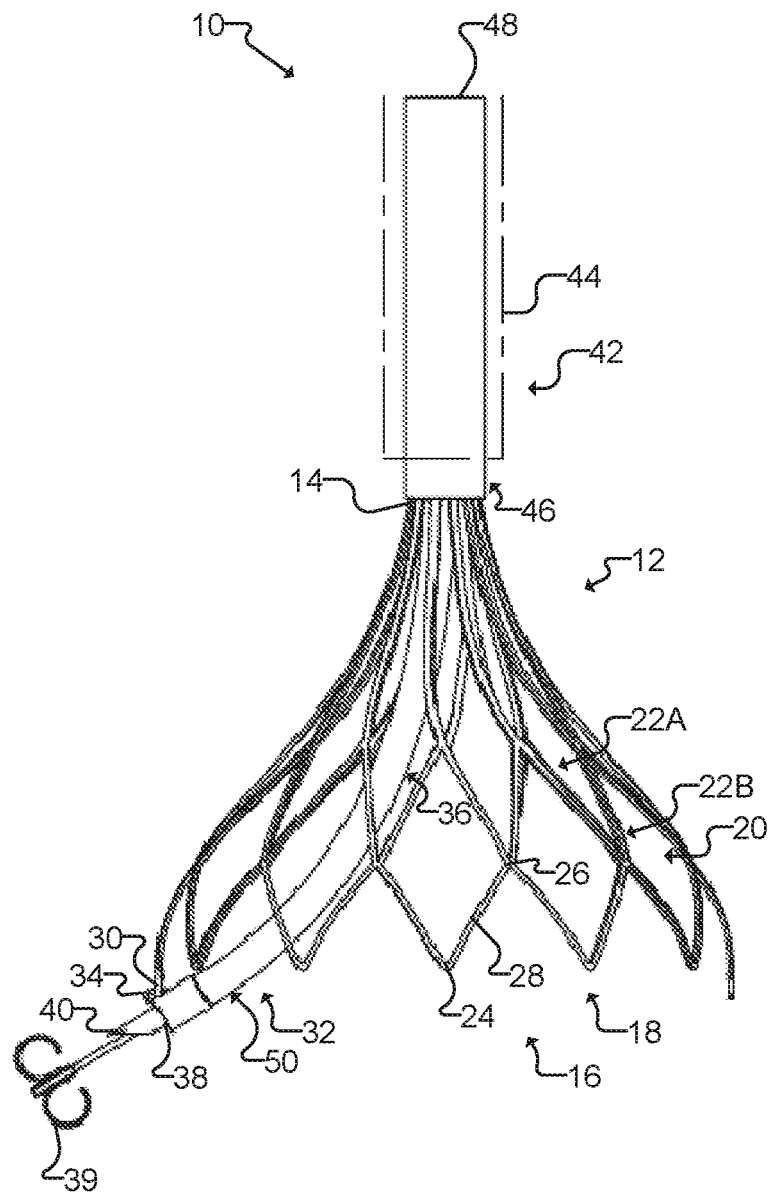
FIG. 3 is a front, perspective view of the device of FIG. 1, showing the expandable structure secured to a stabilizer catheter and a delivery catheter.

In example embodiments, an attachment member 30 is arranged to secure a catheter 32 to the expandable structure 12. The attachment member 30 may extend distally from the distal edge 18. In an example embodiment, the attachment member 30 extends distally from one of the first terminal ends 24. Referring to FIG. 3, in an example embodiment, the catheter 32 comprises an elongate tubular body 36 extending longitudinally from a proximal end (not shown) to a distal end 38. The tubular body 36 may be made of a flexible material. A distal tip 40 may be secured to and extend distally from the distal end 38 of the catheter 32. In some embodiments, the catheter 32 is a delivery catheter, such as an anchor delivery catheter. The anchor delivery catheter 32 may comprise one or more anchors housed within the body 36. Means are provided within the catheter 32 to advance the one or more anchors 39 to a desired implantation location within the body through the distal tip 40.

A connector 34 may be arranged to project from the catheter 32 to engage the attachment member 30. The connector 34 may be positioned near the distal tip 40 of the catheter 32. In some embodiments, the connector 34 is positioned on a surface of the tubular body 36 proximate to the distal end 38. In an example embodiment, the attachment member 30 comprises a closed loop, and the connector 34 comprises a hook. The hook of the connector 34 is dimensioned to engage the corresponding closed loop of the attachment member 30. The attachment member 30 and connector 34 may however be in any other suitable structural forms which allow for secure connection between the expandable structure 12 and the catheter 32.

In some embodiments, when the connector 34 is coupled to the attachment member 30, the distal tip 40 of the catheter 32 is positioned at a point equal to or greater than a radial limit of the expandable structure 12. The radial limit of the expandable structure 12 is defined by a maximum radius of the expandable structure 12 when the expandable structure 12 is in a fully expanded configuration. When the distal tip 40 of the catheter 32 is positioned at a point equal to or greater than the radial limit of the expandable structure 12, the biocompatible materials (such as anchors) that are advanced from the distal tip 40 will be delivered to an implantation location that is positioned at a point at or beyond the radial limit of the expandable structure 12.

In an example embodiment, the tubular body 36 has a curved portion 37 proximate to the distal end 38 of the catheter 32. A single point of connection between the expandable structure 12 and the catheter 32, specifically at their respective distal edge 18 and distal end 38, advantageously allows for accommodating such a catheter (i.e., a catheter with a curved portion at its distal end). A single point of connection also facilitates ease of coupling of the catheter to the device.

Figure 7:
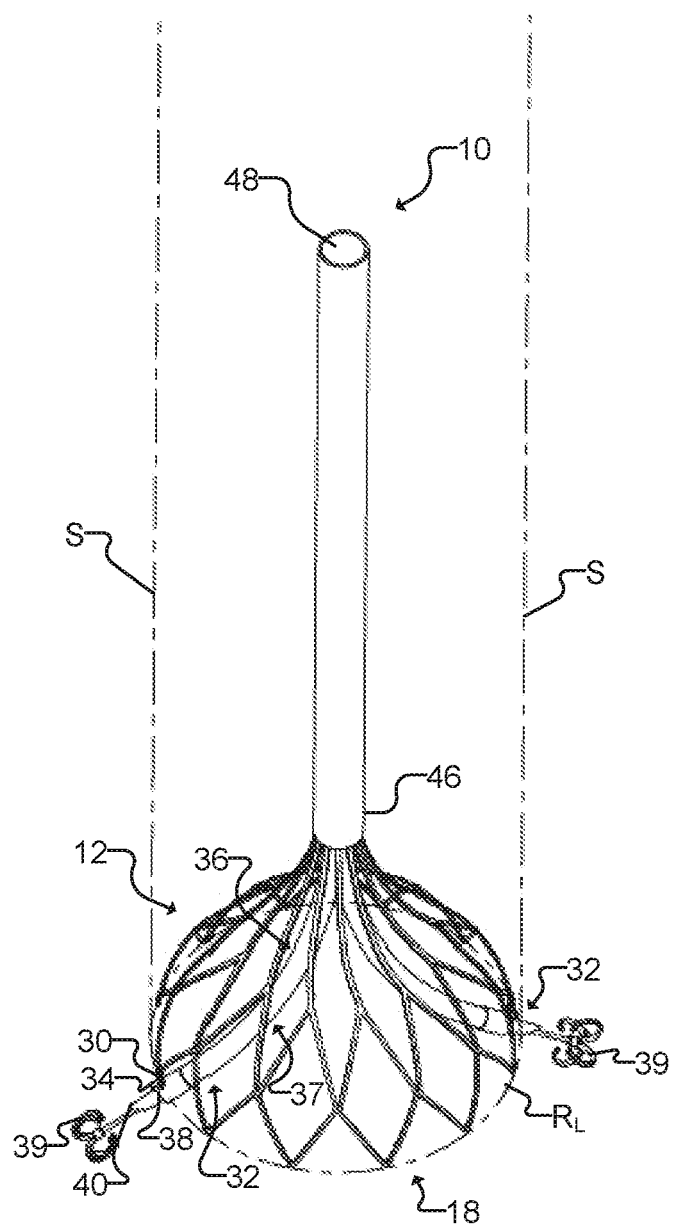
FIG. 7 is a schematic diagram illustrating the device of FIG. 4, depicting an imaginary cylinder to explain a radial limit of the expandable structure.

FIG. 7 schematically illustrates the distal tip 40 of the catheter 32 being positioned at a point greater than a radial limit of the expandable structure 12. In FIG. 7, the radial limit of the expandable structure 12 is referred to as a circular base ($R_L$). When the distal tip 40 of the catheter 32 is at a point greater than a radial limit of the expandable structure 12, an angle greater than zero is created between the curved portion 37 of the catheter 32 and a longitudinal surface (S) of an imaginary cylinder extending longitudinally from the circular base ($R_L$), parallel to the longitudinal axis of the expandable structure 12, in a direction towards the proximal end 14 of the expandable structure 12.

The expandable structure 12 may be secured to a stabilizer catheter 46. The stabilizer catheter 46 may for example be a low profile catheter. The stabilizer catheter 46 may be defined by a hollow body 48. The proximal end 14 of the expansible structure 12 may be secured to an end of the hollow body 48. The stabilizer catheter 46 may extend from the hollow body 48 at its proximal end to the expansible structure 12 at its distal end.

The catheter 32 is insertable through the hollow body 48 of the stabilizer catheter 46, and extends longitudinally towards the attachment member 30 to allow the connector 34 of the catheter 32 to align and couple to the attachment member 30. In the use position, the catheter 32 is located within a central axis of the stabilizer catheter 46.

Figure 5:
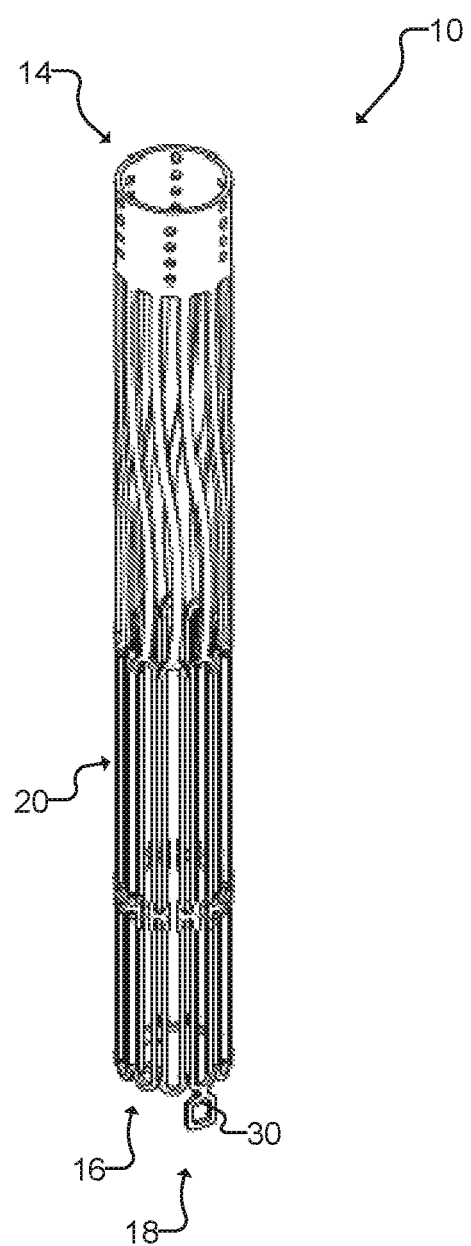
FIG. 5 is an isolated front plan view of the device of FIG. 1, showing the expandable structure in a fully compressed configuration, without a retractable catheter sheath.
Figure 6:
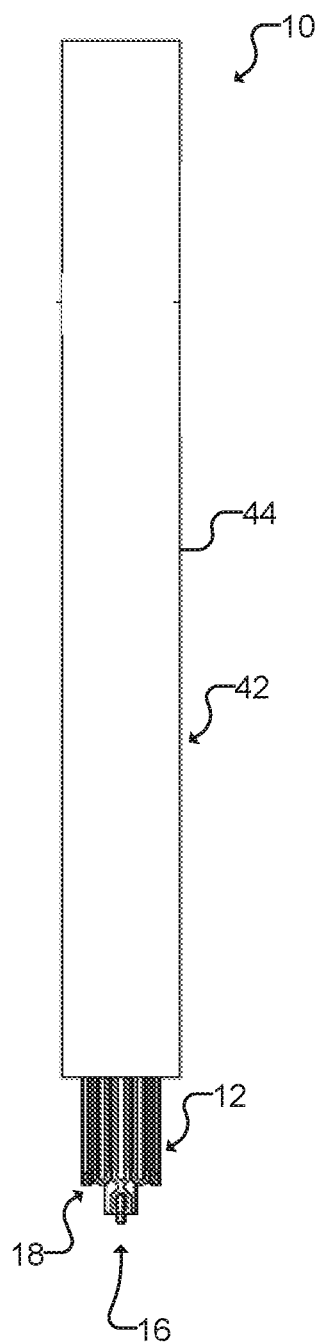
FIG. 6 is an isolated front plan view of FIG. 5, showing the retractable catheter sheath surrounding the expandable structure.

The expandable structure 12 is expandable in a radial direction. Means 42 are provided to radially extend the expandable structure 12 between a compressed configuration and an expanded configuration (see FIGS. 3 and 6). In some embodiments, means 42 comprises a retractable catheter sheath 44. The retractable catheter sheath 44 is moveable along the longitudinal axis of the expandable structure 12 and/or the stabilizer catheter 46, and is dimensioned to radially surround the expandable structure 12 and/or the stabilizer catheter 46. The expandable structure 12 may be fully or partially expanded. The extent of which the expandable structure 12 is expanded corresponds to the amount of retraction of the retractable catheter sheath 44 towards the proximal end 14 of the expandable structure 12. For example, when the expandable structure 12 is fully expanded, the retractable catheter sheath 44 is moved proximally to the proximal end 14 of the expandable structure 12 to be fully withdrawn from the expandable structure 12. When the expandable structure 12 fully compressed, the retractable catheter sheath 44 is moved distally towards the distal end 16 of the expandable structure 12 to fully surround the expandable structure 12. When the expandable structure 12 is partially expanded, the retractable catheter sheath 44 is positioned at a point between the proximal 14 and distal 16 ends. The diameter of the distal edge 18 changes as the expandable structure 12 extends between the fully compressed configuration and the fully expanded configuration. The diameter of the distal edge 18 is at a minimum when the expandable structure 12 is in the fully compressed configuration (see FIGS. 5 and 6), and the diameter of the distal edge 18 is at a maximum when the expandable structure 12 is in the fully expanded configuration.

The expandable structure 12 has a stiffness in an amount sufficient to resist displacement of the device 10 during the advancement of biocompatible materials (e.g., anchors) from the delivery catheter 32. The rigidity of the expandable structure 12 facilitates precise positioning of the delivery catheter 32 to the specific implantation locations in a moving heart. The desired stiffness of the expandable structure 12 can be provided by varying the thickness of the materials used and/or by modifying the configuration of the closed cells 20 (e.g., by reducing or increasing the number of rows of closed cells 20 and/or varying the area of one or more rows of the closed cells 20, etc.).

The expandable structure 12 is made of a biocompatible material. In some embodiments, the expandable structure 12 is made of a material that allows for self-expansion of the structure 12 after retraction of the retractable catheter sheath 44. In some embodiments, the expandable structure 12 is made of a shape memory alloy. An example of a suitable shape memory alloy that can be used is Nitinol.

In the fully expanded configuration, the expandable structure 12 may taper inwardly as it extends from the proximal end 14 to the distal end 16 as best shown in FIG. 3. In some embodiments, the expandable structure 12 comprises either a tulip or cone shape in the fully expanded configuration.

The device 10 may optionally include a cover (not shown) mountable over the expandable structure 12. The cover may be provided to prevent injury to the implantation location.

The device 10 may include means for simultaneously rotating the expandable structure 12 and the delivery catheter 32. In some embodiments, the means for rotating the expandable structure 12 and the delivery catheter 32 further includes simultaneously rotating the stabilizer catheter 46 with the expandable structure 12 and the delivery catheter 32.

Figure 4:
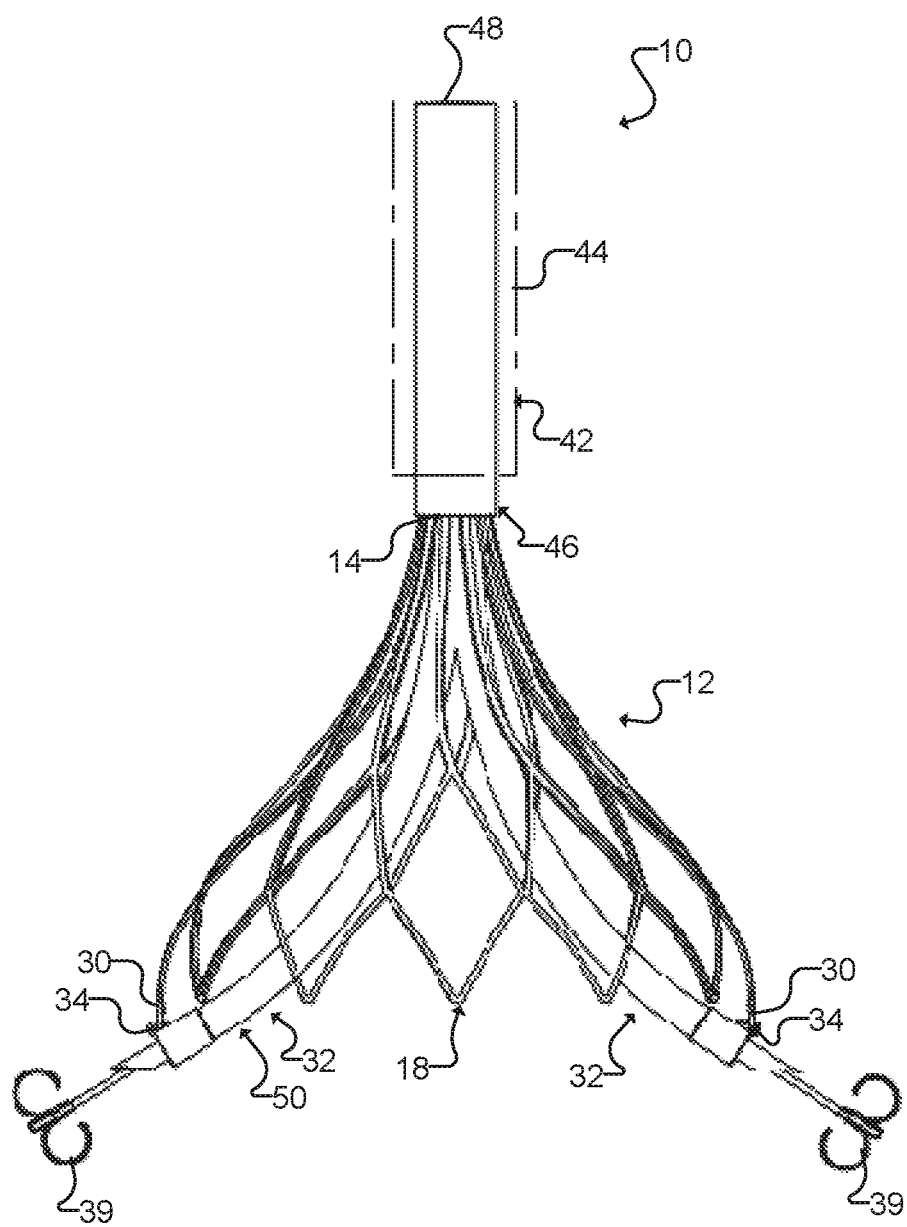
FIG. 4 is a front, perspective view of the device of FIG. 1, showing the expandable structure secured to the stabilizer catheter and to two delivery catheters.

Some embodiments of the device 10 include a plurality of attachment members 30. This is best illustrated in FIG. 4. The attachment members 30 each extends distally from a separate point along the distal edge 18 of the expandable structure 12. The plurality of attachment members 30 may be provided to each couple to a connector 34 projecting from a respective delivery catheter 32. In such embodiments, each of the delivery catheters 32 is inserted within the hollow body 48 of the stabilizer catheter 46. The attachment members 30 may be positioned spaced-apart radially along the distal edge 18. In some embodiments, the device 10 includes two attachment members 30. The two attachment members 30 may for example be positioned diametrically opposed from one another. The two attachment members 30 may each be provided to secure one delivery catheter 32 to the expandable structure 12.

Figure 8A:
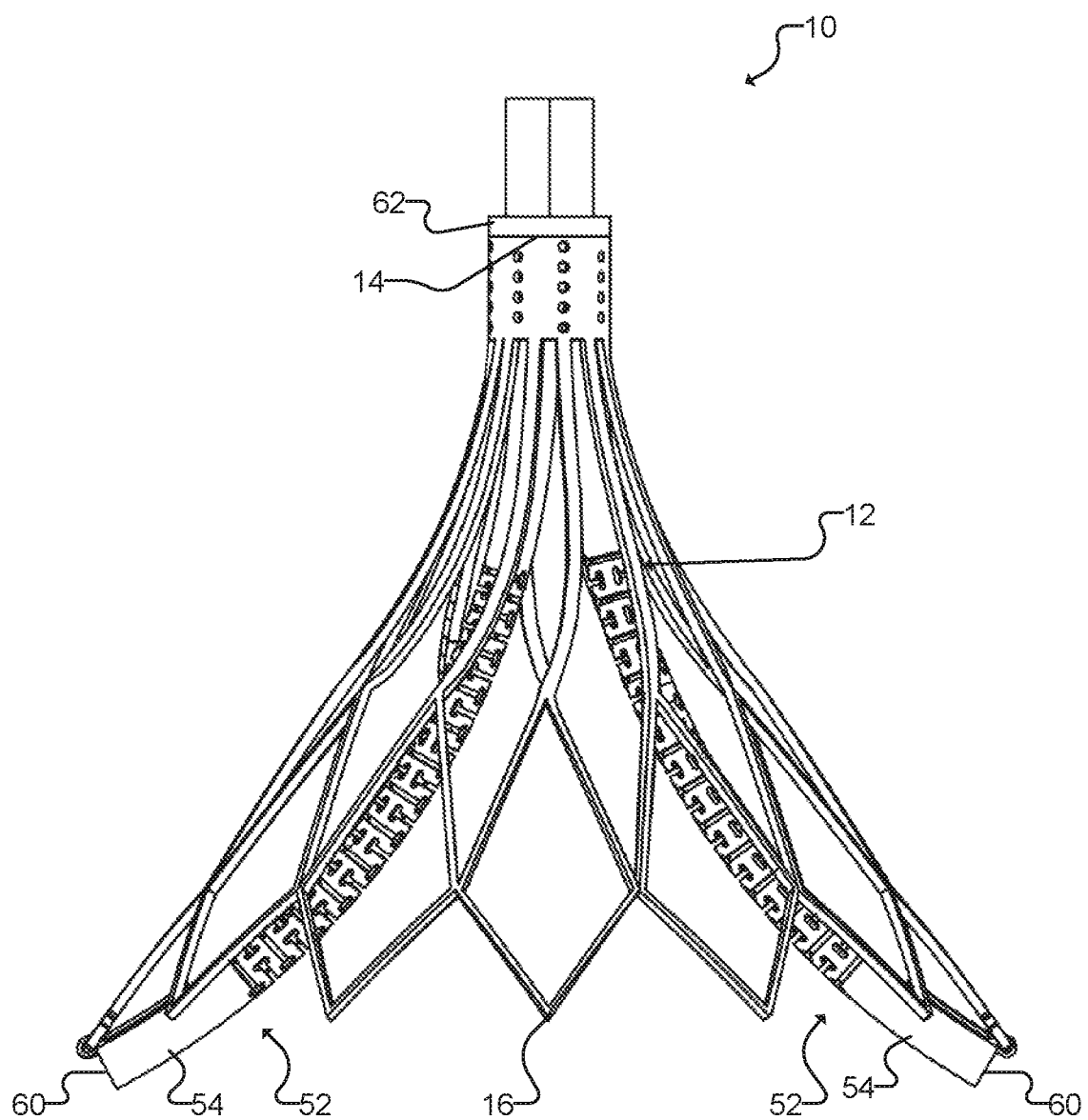
FIG. 8A is an isolated front, perspective view of a device according to a second example embodiment, showing an expandable structure in an expanded configuration secured to two sleeves.
Figure 8B:
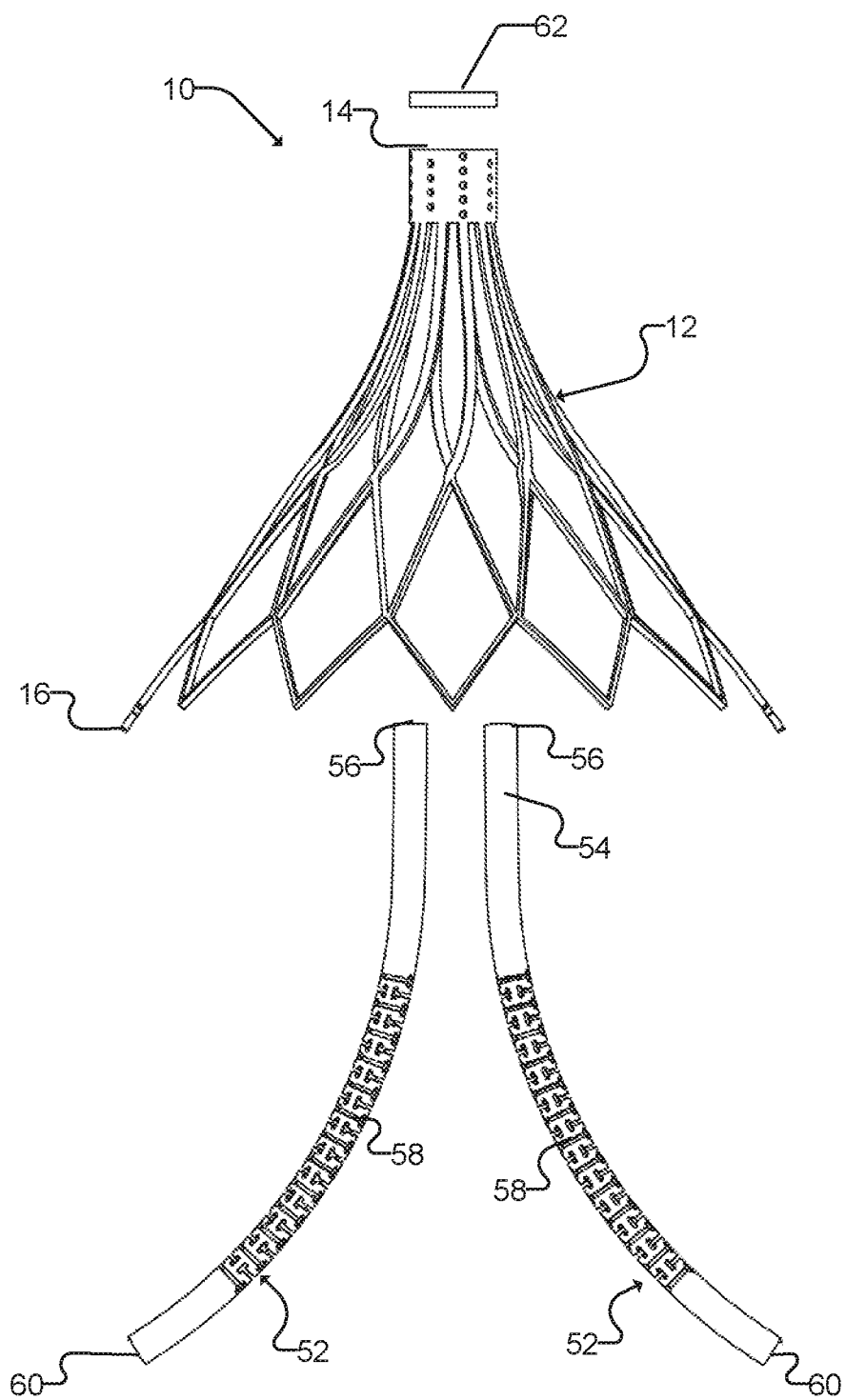
FIG. 8B is an exploded view of FIG. 8A.
Figure 9:
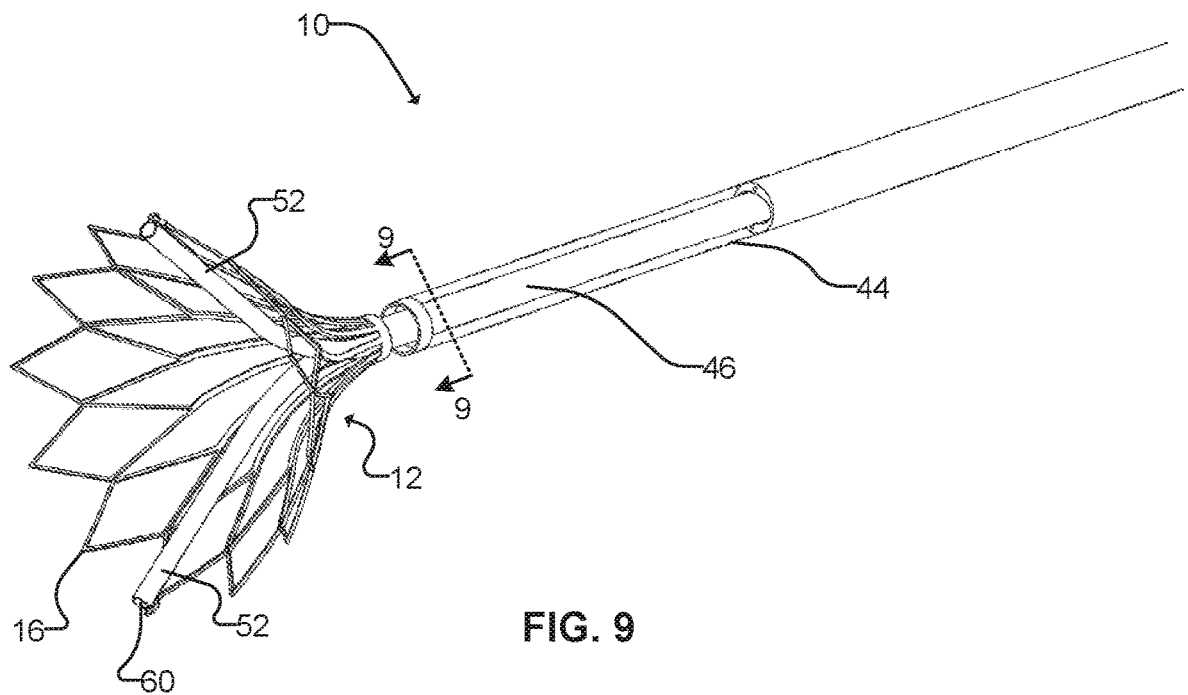
FIG. 9 is a perspective view of the device of FIG. 8A, showing the expandable structure secured to the stabilizer catheter and the retractable catheter sheath surrounding the stabilizer catheter.

Referring to FIGS. 8A, 8B and 9, in some embodiments, the device 10 includes one or more sleeves 52, each having a hollow body 54 through which the delivery catheter 32 is insertable therein. Each of the sleeves 52 extends longitudinally from a proximal end 56 to a distal end 60. When the expandable structure 12 is in a fully compressed configuration, the longitudinal length of each of the sleeves 52, extending from the proximal end 56 to the distal end 60, is approximately equal to the longitudinal length of the expansible structure 12, extending from the proximal end 14 to the distal end 16. When the expandable structure 12 is being extended to an expanded configuration, its longitudinal length decreases, thereby forming a curved region 58 between the proximal end 56 and the distal end 60. The curved region 58 may have a concave shape, shaped to allow the distal end 60 of the sleeve 52 to contact the distal end 16 of the expandable structure 12. The sleeves 52 may be secured to the expandable structure 12. In some embodiments, the sleeves 52 are secured to the expandable structure 12 by welding at least a portion of the sleeve 52 to the expandable structure 12. In the example embodiments, each of the sleeves 52 are secured to the expandable structure 12 by securing the proximal end 56 of each of the sleeves 52 to the proximal end 14 of the expandable structure 12, and the distal end 60 of each of the sleeves to the distal end 16 of the expandable structure 12. A plate 62 may be arranged at the proximal end 14 of the expandable structure 12 for the proximal ends 56 of the sleeves 52 to secure thereto. In such embodiments, the attachment members 30 may be omitted. In other embodiments, the expandable structure 12 includes one or more attachment members 30 arranged to project from the distal end 16 of the expandable structure 12. In such embodiments, each of the sleeves 52 includes at least one connector 34 such a hook arranged to secure to an attachment member 30. Similar to the expandable structure 12, the sleeves 52 may be made of a biocompatible material, such as Nitinol.

Figure 10:
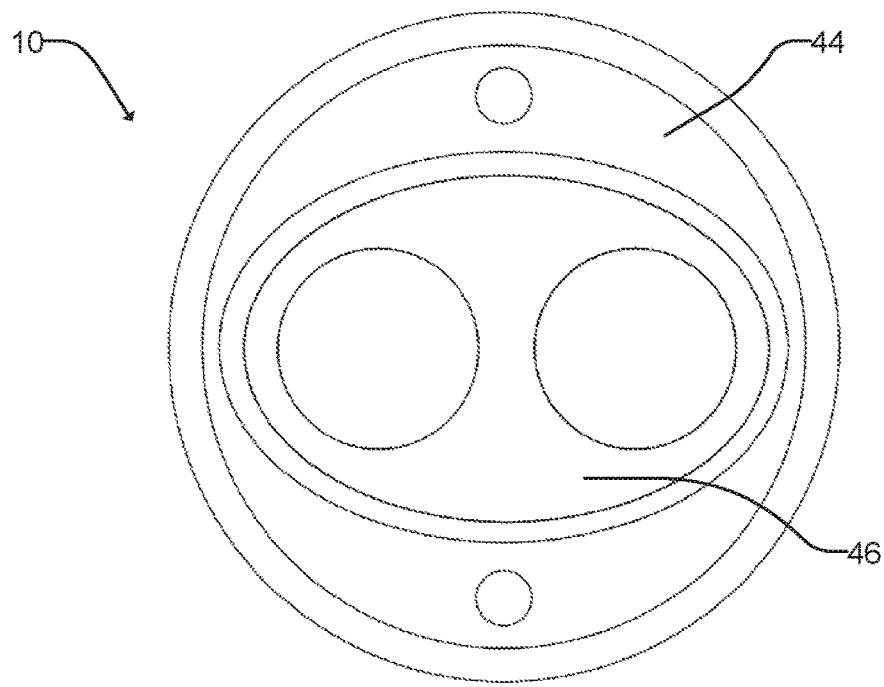
FIG. 10 is a cross-sectional view taken along line 9-9 of FIG. 9.

Referring to FIGS. 9 and 10, in some embodiments, the stabilizer catheter 46 is keyed into the retractable catheter sheath 44 so that when the stabilizer catheter 46 rotates, the catheter sheath 44 is rotated also. This may improve torque response during use.

The invention provides a method of using the device 10. An example method of use includes delivering a biocompatible material to a desired implantation location within a heart of a subject using a stabilizer. The biocompatible material may for example include anchors or pacemaker leads. Any other suitable biocompatible materials may however be delivered by the use of the device 10 to stabilize suitable catheters known in the art. In an example embodiment, the device 10 is used to deliver ventricular anchors in the myocardium in the left ventricles of the heart.

The method may begin with the expandable structure 12 as a standalone tool. In such embodiments, the expandable structure 12 is first secured to an end of the stabilizer catheter 46. In some embodiments, the catheter 32 may insert through the hollow body 48 of the stabilizer catheter 46 and extend distally towards the attachment member 30. The connector 34 of the catheter 32 aligns with and couples to the attachment member 30 to secure the catheter 32 to the expandable structure 12. In other embodiments, the catheter 32 may insert through the hollow body 48 of the stabilizer catheter 46 and the hollow body 54 of the sleeve 52, and extends out of the distal end 60 of the sleeve 52. In some embodiments, the expandable structure 12 is provided with the stabilizer catheter 46 and/or catheter 32 already secured in position. In such embodiments, the steps of securing the expandable structure 12 to the stabilizer catheter 46 and/or the catheter 32 can be eliminated. In some embodiments, more than one catheters 32 are inserted through the hollow body 48 of the stabilizer catheter 46. In such embodiments, a plurality of attachment members 30 are provided, each positioned to couple to a respective one of the catheters 32.

The expandable structure 12 of the device 10 is arranged in a fully compressed configuration by positioning the retractable catheter sheath 44 over the expandable structure 12 prior to advancement into a body of a subject. In an example embodiment, the device is advanced to the left atrium of the heart via transfemoral and/or transseptal access, across the mitrel valve to reach a desired region. The desired region is proximate to the desired implantation location. In some embodiments, the desired region is below the papillary muscle tips. In such embodiments, the desired implantation location is the myocardium.

Once the expandable structure 12 reaches the desired region, such as below the papillary muscle tips, the retractable catheter sheath 44 is moved in the proximal direction of the expandable structure 12 to partially expand the expandable structure 12. Some embodiments of the method involve rotating the partially expanded expandable structure 12 and/or catheter 32 and/or stabilizer catheter 46 simultaneously to position the catheter 32. Such positioning comprises precisely positioning the distal tip 40 of the catheter 32 at the desired implantation location, such as the mycocardium. Specifically, the distal end 38 of the catheter 38 or the distal end 60 of the sleeve 52 (in embodiments in which the device 10 includes one more sleeves 52) is first brought into contact with the desired region. The distal tip 40 of the catheter 32 is then advanced from the distal end 38 of the delivery catheter 32 or the distal end 60 of the sleeve 52 at the desired implantation location, such as a certain depth into the myocardium.

When the distal tip 40 of the catheter 32 is precisely positioned at the implantation location, the retractable catheter sheath 44 is moved further proximally towards the proximal end 14 of the expandable structure 12 to fully expand the expandable structure 12. In a fully expanded configuration, the expandable structure 12 is in contact with surfaces within the region. In an example use embodiment, the distal edge 18 of the expandable structure 12 fills the ventricular cavity completely or partially when the expandable structure 12 is in a fully expanded configuration. The contact between the expandable structure 12 and the surfaces within the region proximate to the desired implantation location allows the expandable structure 12 and the region to move together as the heart beats with normal ventricular motion. The zero net motion between the expandable structure 12 and the region creates, from the frame of reference of the delivery catheter 32, a motionless implantation location (and vice versa from the frame of reference of the implantation location) thereby stabilizing the catheter 32 against the implantation location. This allows for controlled and atraumatic delivery of biocompatible materials from the delivery catheter 32 into the implantation location while the heart is beating.

In an example use embodiment the catheter 32 is used to deliver one or more ventricular anchors 39 to the myocardium. The catheter 32 may be defined by a hollow body 50 through which the anchor 39 may travel for delivery into the myocardium. The anchor 39 may be delivered directly into the myocardium through the catheter 32. Alternatively the anchor 39 may be advanced within a hollow needle which is embedded into the myocardium. The anchor 39 may optionally include an attached tether and guidewire dimensioned to traverse the vasculature to an external to a subject.

After the biocompatible materials are delivered to the implantation location, the expandable structure 12 may first be compressed in the fully compressed configuration by moving the retractable catheter sheath 44 distally over the expandable structure 12. The device 10 may then be withdrawn from the body of the subject.

The advancement of the device to the desired region and/or implantation location may be guided by echocardiography.

Throughout the foregoing description and the drawings, in which corresponding and like parts are identified by the same reference characters, specific details have been set forth in order to provide a more thorough understanding to persons skilled in the art. However, well known elements may not have been shown or described in detail or at all to avoid unnecessarily obscuring the disclosure.

As will be apparent to those skilled in the art in the light of the foregoing disclosure, many alterations and modifications are possible in the practice of this invention without departing from the scope thereof. Accordingly, the description and drawings are to be regarded in an illustrative, rather than a restrictive, sense.

The invention claimed is:

1. A device for stabilizing a delivery catheter, comprising:
   a radially expandable structure extending from a proximal end to an opposing distal end along a longitudinal axis thereof, the distal end defining a distal edge and wherein the proximal end is secured to a stabilizer catheter;
   means for positioning the delivery catheter, wherein the means for positioning the delivery catheter comprises at least one sleeve extending from a proximal end to a distal end, wherein at least one of the proximal end and the distal end of the sleeve being fixedly secured to the expandable structure, and wherein the sleeve is arranged for the delivery catheter to be insertable therethrough; and
   a retractable catheter sheath moveable along the longitudinal axis of the expandable structure to extend the expandable structure between a compressed configuration and an expanded configuration.

2. The device according to claim 1, wherein the proximal end of the sleeve is secured to the proximal end of the expandable structure, and the distal end of the sleeve is secured to the distal end of the expandable structure.

3. The device according to claim 2, wherein the sleeve is secured to the expandable structure by welding.

4. The device according to claim 1, wherein when the expandable structure is in the expanded configuration, the sleeve further comprises a curved region, extending between the proximal end and the distal end, and wherein the curved region comprises a concave shape.

5. The device according to claim 1, further comprising a plate arranged at the proximal end of the expandable structure, wherein the proximal end of the sleeve is secured to the plate.

6. The device according to claim 1, wherein a radial limit of the expandable structure is equal to a maximum radius of the expandable structure when the expandable structure is in a fully expanded configuration.

7. The device according to claim 1, wherein the stabilizer catheter comprises a hollow tube with a proximal end and an opposing distal end, the expandable structure being secured to the distal end of the stabilizer catheter.

8. The device according to claim 1, wherein the expandable structure comprises a plurality of closed cells arranged radially in one or more rows.

9. The device according to claim 1, wherein the distal end of the expandable structure tapers radially inwardly when the expandable structure is in the expanded configuration.

10. The device according to claim 1, wherein the at least one sleeve comprises a plurality of sleeves, each of the sleeves arranged to position one of the delivery catheters.

11. The device according to claim 10, wherein the at least one sleeve comprises two sleeves arranged diametrically opposed to each other.

12. A device for stabilizing a delivery catheter, comprising:
a radially expandable structure extending from a proximal end to an opposing distal end along a longitudinal axis thereof, the distal end defining a distal edge and wherein the proximal end is secured to a stabilizer catheter; means for positioning the delivery catheter, wherein the means for positioning the delivery catheter comprises at least one sleeve extending from a proximal end to a distal end, wherein the distal end of the sleeve is secured to the expandable structure by coupling to an attachment member projecting from the distal edge of the expandable structure, and wherein the sleeve is arranged for the delivery catheter to be insertable therethrough; and a retractable catheter sheath moveable along the longitudinal axis of the expandable structure to extend the expandable structure between a compressed configuration and an expanded configuration.

* * * * *